United States Patent [19]

Pomper et al.

[11] 4,232,045

[45] Nov. 4, 1980

[54] PREPARATION OF FREE-FLOWING PARTICULATE YEAST

[75] Inventors: Seymour Pomper, Stamford, Conn.; Emanuel Akerman, Bronx, N.Y.

[73] Assignee: Standard Brands Incorporated, Wilton, Conn.

[21] Appl. No.: 839,865

[22] Filed: Oct. 6, 1977

[51] Int. Cl.$^2$ ............................................. C12C 11/26
[52] U.S. Cl. ....................................... 426/62; 426/19; 426/656; 435/256
[58] Field of Search .................... 426/60, 62, 656, 19; 195/74, 97, 98; 435/256

[56] References Cited

U.S. PATENT DOCUMENTS

| | | | |
|---|---|---|---|
| 1,420,557 | 6/1922 | Klein | 195/74 |
| 3,023,104 | 2/1962 | Battista | 426/549 |
| 3,780,181 | 12/1973 | Trevelyan | 195/98 X |
| 4,160,040 | 7/1979 | Luca et al. | 426/62 |

FOREIGN PATENT DOCUMENTS

| | | | |
|---|---|---|---|
| 2651349 | 5/1977 | Fed. Rep. of Germany . | |
| 1397410 | 6/1975 | United Kingdom | 426/62 |
| 1459407 | 12/1976 | United Kingdom . | |

*Primary Examiner*—David M. Naff

[57] ABSTRACT

A free-flowing particulate yeast is provided comprising baker's yeast and a minor amount of a solid, substantially non-deliquescent drying agent having a particle size of less than about 100 milli-microns. Preferred drying agents are hydrophilic silicon dioxide, micronized wood pulp and micronized cellulose. The drying agent is dispersed throughout the yeast and the amount thereof utilized is sufficient to bind or absorb a portion of the extracellular water without substantially deleteriously affecting the leavening activity of the yeast. The drying agent maintains the flowability of the particulate yeast over extended periods.

4 Claims, No Drawings

PREPARATION OF FREE-FLOWING PARTICULATE YEAST

BACKGROUND OF THE INVENTION

This invention relates to a particulate yeast product having improved flowability characteristics. More particularly, this invention relates to a particulate yeast product, commonly referred to as bulk yeast, having improved flowability characteristics.

DESCRIPTION OF THE PRIOR ART

Yeast which is to be used for baking purposes is produced on a commercial scale by a multi-stage operation. This multi-stage operation includes, generally, a first step of preparing the basic ingredients needed by the yeast for growth. The basic ingredients may include sterilized cane sugar and/or molasses, corn steep liquor and an acid or alkali to adjust the pH of the mixture to the range of from 4 to 5. The mixture is diluted with water, fortified by the addition of inorganic nitrogen- and phosphorous-containing compounds and, when necessary, the pH of the mixture is again adjusted to a range of 4 to 5. This mixture is known in the art as "mash."

To attain the high degree of purity required for yeast which is to be used for baking purposes and for other reasons, yeast is grown in stages, starting with seed stages and finishing with growing in fermentors of commercial scale. The yeast is grown under aerobic conditions by the addition of large volumes of air to the growth medium. Carbohydrates and nitrogen sources are continuously incorporated into the mash in the last stages of propagation. The temperature and pH of the growth medium are maintained within ranges where optimum growth of the yeast occurs. After the propagation of the yeast, the yeast is separated from the other constituents of the growth medium by centrifugation, washed and again centrifuged. Yeast at this stage is known in the art as cream yeast. Cream yeast is transferred to a filter where relatively large quantities of its extracellular water are removed. Yeast at this stage is known in the art as compressed yeast containing approximately 70 percent moisture and may be molded or extruded into blocks or cubes in which form it is supplied to bakers and consumers. Another yeast product commonly supplied to bakers is bulk yeast. Bulk yeast is compressed yeast which has been granulated to provide substantially uniform particles and is generally packaged in fifty pound bags.

Baker's yeast comprises a mass of living yeast cells having varying amounts of extracellular water in the interstitial spaces between and surrounding the cells. Water is also a major component of the yeast cell composition and is commonly referred to as internal or intracellular water. The relative amounts of water inside of and external to the cells are governed in large part by equilibrium conditions. If the osmotic pressure of the fluid surrounding the cells is greater than that of the fluid within the cells, water will pass through the cell membranes into the extracellular spaces and, conversely, extracellular water will pass into the cells if a greater osmotic pressure exists therein.

The consistency, i.e., the relative dryness or wetness of yeast is determined largely by the relationship between intracellular and extracellular water. The greater the proportion of extracellular water, the wetter will be the consistency of the yeast and vice versa. Within limits, the wetter the consistency of the yeast, the greater will be the tendency for the yeast to coalesce and exhibit decreased flowability.

Bulk yeast finds its greatest application in baking operations which employ continuous systems where the required ingredients may be flowed or metered upon demand. Compressed yeast is difficult to utilize in continuous systems while bulk yeast, due to its flowability characteristics, generally meets the requirements of such systems.

At least several weeks will frequently intervene between the time bulk yeast is packaged and when it is used. In common with all living organisms, the yeast cell respires during storage, one of the end products of such respiration being water. The yeast cell membrane permits free passage of water into and out of the cell and, depending upon the relative conditions of osmolarity on either side of the membrane, the extracellular water content of bulk yeast may increase sufficiently under storage conditions to adversely affect the flowability characteristics of the yeast. This problem may be accentuated when storage conditions are less than optimal as, for example, when bags containing the yeast are stacked or the yeast is exposed to high temperatures or freezing conditions.

One approach to the problem of imparting improved flowability to bulk yeast is to dry the yeast to a lower initial water level, e.g., 65 percent or below. Although this procedure is fairly effective in terms of providing a satisfactory product, it entails additional energy and labor expenditures and thereby adds to the cost of the yeast. Moreover, a decrease in the water content of the yeast obviously mandates a concomitant increase in the amount of yeast solids in the bulk product. Also, from a manufacturing standpoint, it is advantageous to run all dewatering filters under the same operating conditions and then subdivide the yeast downstream from the filters into the bulk and compressed yeast rather than maintain separate facilities for each.

OBJECTS OF THE INVENTION

It is the principal object of the present invention to provide a particulate yeast product having improved flowability characteristics. Other objects of the invention will be apparent from the following description and the appended claims.

SUMMARY OF THE INVENTION

A free-flowing particulate yeast product is produced. The product comprises baker's yeast and a minor amount of a solid, substantially non-deliquescent drying agent having a particle size of less than about 100 millimicrons dispersed throughout the yeast. The amount of drying agent is sufficient to bind or absorb a portion of the extracellular water without substantially deleteriously affecting the leavening activity of the yeast. The drying agent maintains the flowability of the yeast over extended periods.

DETAILED DESCRIPTION OF THE INVENTION

The term "non-deliquescent drying agent" as utilized herein refers to a solid particulate material which has the inherent property of binding or absorbing a portion of the extracellular water present in yeast without becoming solubilized therein. It is preferred that the particle size of the drying agent be less than about 100 millimicrons so that it can be thoroughly dispersed throughout the yeast. Additionally, the agent will bind or absorb additional extracellular water which is formed during respiration of the yeast over extended periods of storage and thus maintain it in a free-flowing condition.

We have found that a variety of materials may act as "non-deliquescent drying agents" in the composition and method of the present invention. Sub-micronized wood pulp, cellulose, fumed or precipated silica and various other silicates have been found to be effective in achieving the objectives of the present invention.

While the typical particle size of the drying agents will be less than about 100 milli-microns it is preferred to utilize an agent having a particle size of from about 10 to about 30 milli-microns.

Typically, prior to contacting or treating the yeast with the drying agent, the yeast will be granulated to average particle size not greater than about 0.25 inches in diameter and preferably will be granulated to a particle size of from about 0.04 to about 0.15 inches in diameter. Granulation may be affected by any suitable means such as grinding, pulverizing, screening, etc. The above-noted particle sizes approximate those attained by passing the yeast through U.S. No. 3, 16 and 6 screens, respectively.

Apparently, a relationship exists between the particle sizes of the drying agent and the yeast. If the yeast particles are too large, the drying agent cannot effectively contact the yeast cells to bind or absorb the requisite amount of extracellular water. On the other hand, if the particle size of the drying agents is too large, distribution thereof throughout the yeast is difficult to attain. Microscopic examination of the treated yeast indicates that it is apparently not necessary for the drying agent to uniformly contact all the yeast cells. Thus, satisfactory results have been obtained in commercial practice when the drying agent was metered onto the yeast from a dispenser disposed above a screw conveyor along which the yeast was transported. On a laboratory scale, shaking a mixture of the yeast and the agent in a mason jar or the like for a period sufficient to thoroughly disperse the agent throughout the yeast has proven satisfactory.

The moisture content of the granulated yeast to be treated with the drying agent will typically be in the range of from about 65 to about 70 percent and preferably of from about 68 to about 69 percent based on the weight of the bulk yeast.

The amount of drying agent utilized will preferably be less than about 3 percent based upon the weight of the bulk yeast and most preferably will be from about 0.5 to about 2 percent on the same weight basis.

Another property which may be imparted to the yeast by the drying agent is color stability, that is, the light tan color of bulk yeast will be maintained during storage and, in certain instances, will actually be lighter than the color of a particulate yeast product prior to the treatment with the drying agent.

In order to more clearly describe the nature of the present invention, specific examples will hereinafter be described. It should be understood, however, that this is done solely by way of example and is not intended to delineate the scope of the invention or limit the ambit of the appended claims.

EXAMPLE I

This Example illustrates the effects of treating bulk yeast with sub-micronized wood pulp (Solka-Floc 200 BWNF manufactured by Brown Co., New York, N.Y.) and a sub-micronized cellulose product (Avicel pH 101, manufactured by FMC Corp., Newark, Del.)

Bulk yeast having an average particle size of about 0.05 inches in diameter and a moisture content of 69.5 percent was treated with the wood pulp at levels of 1,2 and 3 percent and with the cellulose product at a level of 2 percent based on the weight of the bulk yeast. The yeast and the above-noted materials were combined in mason jars and the jars shaken vertically thirty times to distribute the material throughout the yeast.

The treated yeast and the untreated bulk yeast serving as control were subjectively assessed for flowability and tactile impression or "feel." The yeasts treated with both Solka-Floc and Avicel were judged to have markedly improved flowability over the untreated yeast and to feel dry to the touch. The leavening activity of the treated and untreated yeast was determined by means of sweet dough punch tests utilizing freshly prepared yeast and yeast which had been stored for three days at 77° F. This means of evaluating the leavening activity of yeast is well known in the art and involves preparing a sweet dough having present a known quantity of yeast, allowing it to rise to a predetermined volume, punching the dough down, allowing it to rise again to the same volume, punching it down and again allowing it to rise to the predetermined volume. The time required for the sweet dough to rise to the predetermined volume is measured and indicates the activity of the yeast—the shorter the required time, the better the activity of the yeast.

The term "sweet dough" as used herein refers to a dough formula containing from 15 to 25 percent, and preferably about 20 percent, sucrose by weight of the flour present.

The results are shown in Table I below:

TABLE I

| | Results of Sweet Dough Punch Tests Utilizing Treated and Untreated Bulk Yeast | | | | |
|---|---|---|---|---|---|
| Treated Preparation | Control (Untreated) (minutes) | Solka-Floc Treated Yeast | | | Avicel Treated Yeast 2% (minutes) |
| | | 1% (minutes) | 2% | 3% | |
| Bulk Yeast (fresh) | 96-54-47 | 96-53-46 | 97-53-44 | 100-54-45 | 101-54-45 |
| Bulk Yeast (stored) | 135-74-65 | 130-72-61 | 134-72-64 | 130-70-62 | 139-72-62 |

As shown by the data in Table I, the leavening activity of the treated yeasts was comparable to that of the untreated yeast.

Example II

This Example illustrates the preparation of a bulk yeast product comprising baker's yeast and a solid, substantially non-deliquescent drying agent.

Baker's yeast having a moisture content of from about 68 to about 70 percent by weight was granulated through a paddle-type mixer to a particle size not greater than about 0.05 inches in diameter. Two percent by weight powdered hydrophilic silicon dioxide (Zeofree 80 manufactured by J. M. Huber Corp., Edison, N.J.) was metered onto the granulated yeast as the yeast moved along a screw conveyor which provided a thorough mixing action so that the yeast particles were substantially coated with the silicon dioxide. The bulk yeast product which was judged to have excellent appearance and color was free-flowing and dry to the touch.

Example III

This Example illustrates the storage stability of the bulk yeast of the present invention in comparison to that of bulk yeast which had not been treated with a solid, substantially non-deliquescent drying agent.

A batch of untreated bulk yeast was granulated and divided into two portions. One portion was treated with powdered silicon dioxide as described in Example II and the second portion served as untreated control. Fifty pound aliquots of the treated and untreated yeasts were separately packaged in numbered, multi-wall bags. The bags were placed in a refrigerator maintained at 35° to 40° F. and representative bags were sampled once each week over a four week period for flowability and leavening activity as determined by sponge and sweet dough punch tests. In carrying out sponge dough punch tests, yeast is incorporated into a sugar-free dough which is allowed to rise and the time required to attain a predetermined volume is measured. The sponge is then made into a typical bread dough containing about 9 percent sugar and the time required to attain a predetermined volume again measured. The sweet dough punch tests were carried out as described in Example I except that the dough was punched down only one time.

The data in Table II indicate that both the treated and untreated bulk yeast maintained adequate leavening activity during the refrigerated storage period. However, the treated yeast remained particulate, free-flowing and dry to the touch while the untreated yeast contained lumps of moist bulk yeast and did not flow evenly from the bags.

The terms and expressions which have been employed are used as terms of description and not of limitation, and it is not intended by the use of such terms and expressions to exclude any equivalents of the features shown and described or portions thereof, since it is recognized that various modifications are possible within the scope of the invention claimed.

TABLE II

Effect of Up to 4 Weeks Refrigeration on Leavening Activity of Bulk Yeast Treated with 2% by Weight Silicon Dioxide

| SAMPLE | % INITIAL MOISTURE | SPONGE DOUGH | | | | | SWEET DOUGH | | | | |
|---|---|---|---|---|---|---|---|---|---|---|---|
| | | 0 WEEK | 1 WEEK | 2 WEEKS | 3 WEEKS | 4 WEEKS | 0 WEEK | 1 WEEK | 2 WEEKS | 3 WEEKS | 4 WEEKS |
| Control (no drying agent) | | | | | | | | | | | |
| Bag #18 | 68.2 | 63/61 | 63/52 | 63/45 | 63/55 | 67/40 | 72/45 | 92/52 | 103/52 | 123/56 | 141/61 |
| Bag #28 | 68.3 | 63/58 | 61/52 | 63/54 | 63/54 | 67/52 | 76/43 | 114/56 | 105/52 | 111/67 | 117/54 |
| Bag #32 | 68.8 | 57/56 | 61/52 | 63/53 | 60/55 | 67/53 | 86/46 | 90/52 | 100/49 | 117/52 | 113/59 |
| Bag #35 | 68.0 | 57/59 | 59/54 | 63/53 | 60/52 | 63/53 | 86/46 | 92/49 | 98/47 | 117/52 | 108/51 |
| Zeofree (2% SiO$_2$) | | | | | | | | | | | |
| Bag #3 | 68.9 | 68/57 | 65/60 | 59/56 | 65/59 | 59/58 | 78/41 | 86/42 | 104/50 | 117/55 | 131/58 |
| Bag #13 | 68.6 | 66/59 | 67/48 | 60/52 | 64/53 | 62/58 | 78/45 | 86/46 | 118/56 | 119/57 | 150/69 |
| Bag #29 | 68.1 | 58/52 | 62/50 | 61/55 | 58/53 | 58/53 | 80/44 | 93/45 | 105/63 | 131/56 | 142/68 |
| Bag #33 | 68.2 | 55/51 | 65/52 | 62/51 | 57/52 | 59/53 | 80/42 | 91/48 | 107/61 | 119/53 | 140/57 |
| Bag #43 | 68.9 | 59/54 | 66/50 | 66/55 | 61/52 | 60/45 | 83/46 | 93/49 | 102/51 | 130/56 | 126/56 |
| Bag #48 | 66.8 | 59/54 | 54/48 | 59/56 | 57/55 | 60/45 | 79/56 | 86/44 | 93/50 | 91/45 | 113/51 |

What is claimed is:

1. A process for preparing a free-flowing particulate bulk yeast product consisting assentially of incorporating into bulk baker's yeast having a moisture content of from about 65 to about 70 percent from about 0.5 to about 3 percent, based on the weight of bulk yeast being treated, of a drying agent having a particle size of less than about 100 milli-microns selected from the group consisting of powdered hydrophilic silicon dioxide, micronized wood pulp and micronized cellulose to produce a bulk yeast product having improved flowability without further drying.

2. A process for preparing a free-flowing particulate bulk yeast product as defined in claim 1, wherein prior to treating the yeast with the drying agent the yeast is granulated to an average particle size not greater than about 0.25 inches in diameter.

3. A process for preparing a free-flowing particulate bulk yeast product as defined in claim 2, wherein prior to treating the yeast with the drying agent the yeast is granulated to an average particle size in the range of from about 0.04 to about 0.15 inches in diameter.

4. A free-flowing particulate bulk yeast product prepared by the process defined in claim 1.

* * * * *